US008546622B2

(12) United States Patent
Jevtic et al.

(10) Patent No.: US 8,546,622 B2
(45) Date of Patent: *Oct. 1, 2013

(54) PROCESS FOR MAKING ETHANOL FROM ACETIC ACID USING ACIDIC CATALYSTS

(75) Inventors: Radmila Jevtic, Houston, TX (US);
Victor J. Johnston, Houston, TX (US);
R. Jay Warner, Houston, TX (US);
Heiko Weiner, Pasadena, TX (US)

(73) Assignee: Celanese International Corporation, Dallas, TX (US)

( * ) Notice: Subject to any disclaimer, the term of this patent is extended or adjusted under 35 U.S.C. 154(b) by 370 days.

This patent is subject to a terminal disclaimer.

(21) Appl. No.: 12/911,457

(22) Filed: Oct. 25, 2010

(65) Prior Publication Data
US 2011/0082322 A1 Apr. 7, 2011

Related U.S. Application Data

(63) Continuation-in-part of application No. 12/699,024, filed on Feb. 2, 2010, and a continuation-in-part of application No. 12/698,947, filed on Feb. 2, 2010, and a continuation-in-part of application No. 12/588,727, filed on Oct. 26, 2009, now Pat. No. 8,309,772, and a continuation-in-part of application No. 12/221,141, filed on Jul. 31, 2008, now Pat. No. 8,863,489, and a continuation-in-part of application No. 12/852,227, filed on Aug. 6, 2010, now Pat. No. 8,309,773, application No. 12/911,457, which is a continuation-in-part of application No. 12/852,269, filed on Aug. 6, 2010, now Pat. No. 8,304,586.

(60) Provisional application No. 61/300,815, filed on Feb. 2, 2010, provisional application No. 61/332,696, filed on May 7, 2010, provisional application No. 61/332,699, filed on May 7, 2010.

(51) Int. Cl.
C07C 29/149 (2006.01)
(52) U.S. Cl.
USPC .......................... 568/885; 568/913; 568/918
(58) Field of Classification Search
USPC .......................................... 568/885, 913, 918
See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,136,704 A | 11/1938 | Mitchell |
| 2,425,389 A | 8/1947 | Oxley et al. |
| 2,549,416 A | 4/1951 | Brooks |
| 2,607,807 A | 8/1952 | Ford |
| 2,649,407 A | 8/1953 | Harrison et al. |
| 2,702,783 A | 2/1955 | Harrison et al. |
| 2,744,939 A | 5/1956 | Kennel et al. |
| 2,801,209 A | 7/1957 | Muller et al. |
| 2,859,241 A | 11/1958 | Schnizer |
| 2,882,244 A | 4/1959 | Milton |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Adam et al. |
| 3,702,886 A | 11/1972 | Araguer |
| 3,729,429 A | 4/1973 | Robson |
| 3,864,284 A | 2/1975 | Clippinger et al. |
| 3,953,524 A | 4/1976 | Steiner |
| 3,990,952 A | 11/1976 | Katzen et al. |
| 4,052,467 A | 10/1977 | Mills et al. |
| 4,065,512 A | 12/1977 | Cares |
| 4,199,438 A | 4/1980 | Antos |
| 4,228,307 A | 10/1980 | Zimmerschied |
| 4,270,015 A | 5/1981 | Knifton |
| 4,275,228 A | 6/1981 | Gruffaz |
| 4,306,942 A | 12/1981 | Brush et al. |
| 4,317,918 A | 3/1982 | Takano et al. |
| 4,319,058 A | 3/1982 | Kulprathipanja et al. |
| 4,328,373 A | 5/1982 | Strojny |
| 4,337,351 A | 6/1982 | Larkins, Jr. |
| 4,374,265 A | 2/1983 | Larkins, Jr. |
| 4,379,028 A | 4/1983 | Berg et al. |
| 4,395,576 A | 7/1983 | Kwantes et al. |
| 4,398,039 A | 8/1983 | Pesa et al. |
| 4,399,305 A | 8/1983 | Schreck |
| 4,421,939 A | 12/1983 | Kiff et al. |
| 4,422,903 A | 12/1983 | Messick et al. |
| 4,426,541 A | 1/1984 | King |
| 4,443,639 A | 4/1984 | Pesa et al. |
| 4,454,358 A | 6/1984 | Kummer et al. |

(Continued)

FOREIGN PATENT DOCUMENTS

CN 1230458 10/1999
CN 102228831 11/2011

(Continued)

OTHER PUBLICATIONS

Subramani et al., "A Review of Recent Literature to Search for an Efficient Catalytic Process for the Conversion of Syngas to Ethanol," Energy & Fuels, 2008, vol. 22, pp. 814-839.
Spivey et al., "Heterogeneous catalytic synthesis of ethanol from biomass-dervied syngas," Chemical Society Review, 2007, vol. 36, pp. 1514-1528.
Hilmen, "Separation of Azeotropic Mixtures: Tools for Analysis and Studies on Batch Distillation Operation" (Nov. 2000) p. 17-20.
Djerboua, et al., "On the performance of a highly loadedCO/SiO2 catalyst in the gas phase hydrogenation of crotonaldehyde thermal treatments—catalyst structure-selectivity relationship," Applied Catalysis A: General (2005), 282, p. 123-133.
Liberkova, and Tourounde, "Performance of Pt/SnO2 catalyst in the gas phase hydrogenation of crotonaldehyde," J. Mol. Catal. A: Chemical (2002), 180, p. 221-230.
Rodrigues and Bueno, "Co/SiO2 catalysts for selective hydrogenation of crotonaldehyde: III. Promoting effect of zinc," Applied Catalysis A: General (2004), 257, p. 210-211.
Ammari, et al. "An emergent catalytic material: Pt/ZnO catalyst for selective hydrogenation of crotonaldehyde," J. Catal. (2004), 221, p. 32-42.

(Continued)

Primary Examiner — Elvis O Price

(57) ABSTRACT

A process for selective formation of ethanol from acetic acid by hydrogenating acetic acid in the presence of a catalyst comprises a first metal on an acidic support. The acidic support may comprise an acidic support material or may comprise an support having an acidic support modifier. The catalyst may be used alone to produced ethanol via hydrogenation or in combination with another catalyst. In addition, the crude ethanol product is separated to obtain ethanol.

11 Claims, 4 Drawing Sheets

(56) References Cited

U.S. PATENT DOCUMENTS

| | | |
|---|---|---|
| 4,465,854 A | 8/1984 | Pond |
| 4,471,136 A | 9/1984 | Larkins |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,521,630 A | 6/1985 | Wattimena |
| 4,541,897 A | 9/1985 | Sommer et al. |
| 4,550,185 A | 10/1985 | Mabry et al. |
| 4,581,473 A | 4/1986 | Polichnowski |
| 4,613,700 A | 9/1986 | Maki |
| 4,620,050 A | 10/1986 | Cognion |
| 4,626,321 A | 12/1986 | Grethlein et al. |
| 4,626,604 A | 12/1986 | Hiles et al. |
| 4,678,543 A | 7/1987 | Houben et al. |
| 4,692,218 A | 9/1987 | Houben et al. |
| 4,696,596 A | 9/1987 | Russell et al. |
| 4,710,086 A | 12/1987 | Naaktgeboren |
| 4,762,817 A | 8/1988 | Logsdon et al. |
| 4,777,303 A | 10/1988 | Kitson et al. |
| 4,804,791 A | 2/1989 | Kitson et al. |
| 4,826,795 A | 5/1989 | Kitson et al. |
| 4,842,693 A | 6/1989 | Wheldon |
| 4,843,170 A | 6/1989 | Isshiki |
| 4,876,402 A | 10/1989 | Logsdon et al. |
| 4,886,905 A | 12/1989 | Larkins, Jr. |
| 4,902,823 A | 2/1990 | Wunder |
| 4,961,826 A | 10/1990 | Grethlein et al. |
| 4,978,778 A | 12/1990 | Isshiki |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,004,845 A | 4/1991 | Bradley et al. |
| 5,008,235 A | 4/1991 | Wegman et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg et al. |
| 5,093,534 A | 3/1992 | Ludwig et al. |
| 5,124,004 A | 6/1992 | Grethlein et al. |
| 5,137,861 A | 8/1992 | Shih et al. |
| 5,144,068 A | 9/1992 | Smith et al. |
| 5,149,680 A | 9/1992 | Kitson et al. |
| 5,155,084 A | 10/1992 | Horn et al. |
| 5,185,308 A | 2/1993 | Bartley |
| 5,185,481 A | 2/1993 | Muto et al. |
| 5,198,592 A | 3/1993 | Van Beijnum et al. |
| 5,233,099 A | 8/1993 | Tabata et al. |
| 5,237,108 A | 8/1993 | Marraccini et al. |
| 5,241,106 A | 8/1993 | Inoue |
| 5,243,095 A | 9/1993 | Roberts et al. |
| 5,250,271 A | 10/1993 | Horizoe et al. |
| 5,292,704 A | 3/1994 | Lester |
| 5,292,916 A | 3/1994 | Matsuzaki et al. |
| 5,306,845 A | 4/1994 | Yokohama |
| 5,334,769 A | 8/1994 | Ferrero et al. |
| 5,348,625 A | 9/1994 | Berg |
| 5,350,504 A | 9/1994 | Dessau |
| 5,415,741 A | 5/1995 | Berg |
| 5,426,246 A | 6/1995 | Nagahara |
| 5,437,770 A | 8/1995 | Berg |
| 5,445,716 A | 8/1995 | Berg |
| 5,449,440 A | 9/1995 | Rescalli et al. |
| 5,475,144 A | 12/1995 | Watson |
| 5,476,827 A | 12/1995 | Ferrero |
| RE35,377 E | 11/1996 | Steinberg |
| 5,585,523 A | 12/1996 | Weiguny |
| 5,599,976 A | 2/1997 | Scates et al. |
| 5,674,800 A | 10/1997 | Abel et al. |
| 5,691,267 A | 11/1997 | Nicolau |
| 5,719,097 A | 2/1998 | Chang et al. |
| 5,719,315 A | 2/1998 | Tustin |
| 5,731,456 A | 3/1998 | Tustin |
| 5,762,765 A | 6/1998 | Berg |
| 5,767,307 A | 6/1998 | Ramprasad |
| 5,770,770 A | 6/1998 | Kim et al. |
| 5,821,111 A | 10/1998 | Grady et al. |
| 5,845,570 A | 12/1998 | Isozaki et al. |
| 5,849,657 A | 12/1998 | Rotgerink |
| 5,861,530 A | 1/1999 | Atkins |
| 5,945,570 A | 8/1999 | Arhancet et al. |
| 5,955,397 A | 9/1999 | Didillon |
| 5,973,193 A | 10/1999 | Crane |
| 5,977,010 A | 11/1999 | Roberts et al. |
| 5,993,610 A | 11/1999 | Berg |
| 6,008,384 A | 12/1999 | Bockrath et al. |
| 6,040,474 A | 3/2000 | Jobson |
| 6,049,008 A | 4/2000 | Roberts |
| 6,093,845 A | 7/2000 | vanAcker |
| 6,114,571 A | 9/2000 | Abel |
| 6,121,498 A | 9/2000 | Tustin |
| 6,143,930 A | 11/2000 | Singh et al. |
| 6,232,352 B1 | 5/2001 | Vidalin |
| 6,232,504 B1 | 5/2001 | Barteau |
| 6,294,703 B1 | 9/2001 | Hara et al. |
| 6,342,464 B1 | 1/2002 | Arhancet et al. |
| 6,375,807 B1 | 4/2002 | Nieuwoudt et al. |
| 6,462,231 B1 | 10/2002 | Yanagawa et al. |
| 6,472,555 B2 | 10/2002 | Choudary |
| 6,476,261 B2 | 11/2002 | Ellis et al. |
| 6,486,366 B1 | 11/2002 | Ostgard |
| 6,495,730 B1 | 12/2002 | Konishi et al. |
| 6,509,180 B1 | 1/2003 | Verser et al. |
| 6,509,290 B1 | 1/2003 | Vaughn |
| 6,521,765 B1 | 2/2003 | Ignatchenko et al. |
| 6,559,333 B1 | 5/2003 | Brunelle |
| 6,603,038 B1 | 8/2003 | Hagemeyer |
| 6,627,770 B1 | 9/2003 | Cheung et al. |
| 6,632,330 B1 | 10/2003 | Colley et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,696,596 B1 | 2/2004 | Herzog |
| 6,723,886 B2 | 4/2004 | Allison et al. |
| 6,727,380 B2 | 4/2004 | Ellis |
| 6,765,110 B2 | 7/2004 | Warner |
| 6,768,021 B2 | 7/2004 | Horan |
| 6,809,217 B1 | 10/2004 | Colley et al. |
| 6,812,372 B2 | 11/2004 | Janssen |
| 6,852,877 B1 | 2/2005 | Zeyss |
| 6,903,045 B2 | 6/2005 | Zoeller |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser |
| 7,084,312 B1 | 8/2006 | Huber |
| 7,115,772 B2 | 10/2006 | Picard et al. |
| 7,208,624 B2 | 4/2007 | Scates et al. |
| 7,297,236 B1 | 11/2007 | Vander Griend |
| 7,351,559 B2 | 4/2008 | Verser et al. |
| 7,351,599 B2 | 4/2008 | Shen |
| 7,375,049 B2 | 5/2008 | Hayes |
| 7,425,657 B1 | 9/2008 | Elliott et al. |
| 7,507,562 B2 | 3/2009 | Verser et al. |
| 7,518,014 B2 | 4/2009 | Kimmich |
| 7,538,060 B2 | 5/2009 | Barnicki et al. |
| 7,553,397 B1 | 6/2009 | Colley et al. |
| 7,572,353 B1 | 8/2009 | Vander Griend |
| 7,608,744 B1 | 10/2009 | Johnston et al. |
| 7,744,727 B2 | 6/2010 | Blum et al. |
| 7,863,489 B2 | 1/2011 | Johnston et al. |
| 7,884,253 B2 | 2/2011 | Stites et al. |
| 7,994,368 B2 | 8/2011 | Johnston et al. |
| 8,071,821 B2 | 12/2011 | Johnston et al. |
| 8,309,772 B2 | 11/2012 | Weiner et al. |
| 2003/0013908 A1 | 1/2003 | Horan |
| 2003/0077771 A1 | 4/2003 | Verser et al. |
| 2003/0104587 A1 | 6/2003 | Verser et al. |
| 2003/0114719 A1 | 6/2003 | Fischer |
| 2003/0191020 A1 | 10/2003 | Bharadwaj |
| 2004/0195084 A1 | 10/2004 | Hetherington et al. |

| | | | | | | |
|---|---|---|---|---|---|---|
| 2004/0232049 | A1 | 11/2004 | Dath et al. | GB | 1559540 | 1/1980 |
| 2006/0019360 | A1 | 1/2006 | Verser et al. | GB | 2136704 | 9/1984 |
| 2006/0102520 | A1 | 5/2006 | Lapinski et al. | JP | 4-193304 | 7/1992 |
| 2006/0106246 | A1 | 5/2006 | Warner | JP | 6116182 | 4/1994 |
| 2006/0127999 | A1 | 6/2006 | Verser et al. | JP | 6116182 A | 4/1994 |
| 2007/0270511 | A1 | 11/2007 | Melnichuk et al. | JP | 10-306047 | 11/1998 |
| 2008/0135396 | A1 | 6/2008 | Blum | JP | 11-147845 | 6/1999 |
| 2008/0207953 | A1 | 8/2008 | Houssin et al. | JP | 2001-046874 | 2/2001 |
| 2008/0257784 | A1 | 10/2008 | Dath et al. | JP | 2001-157841 | 6/2001 |
| 2008/0319236 | A1 | 12/2008 | McNeff et al. | WO | WO 83/03409 | 10/1983 |
| 2009/0005588 | A1 | 1/2009 | Hassan | WO | WO 99/08791 | 2/1999 |
| 2009/0014313 | A1 | 1/2009 | Lee et al. | WO | 2003040037 A1 | 5/2003 |
| 2009/0023192 | A1 | 1/2009 | Verser et al. | WO | WO 03/040263 A2 | 5/2003 |
| 2009/0081749 | A1 | 3/2009 | Verser | WO | WO 2005/102513 | 11/2005 |
| 2009/0166172 | A1 | 7/2009 | Casey | WO | WO 2007/003897 | 1/2007 |
| 2009/0221725 | A1 | 9/2009 | Chornet et al. | WO | WO 2008/135192 | 11/2008 |
| 2009/0318573 | A1 | 12/2009 | Stites et al. | WO | 2009009322 A1 | 1/2009 |
| 2009/0326080 | A1 | 12/2009 | Chornet et al. | WO | 2009009323 A1 | 1/2009 |
| 2010/0016454 | A1 | 1/2010 | Gracey et al. | WO | WO 2009/048335 | 4/2009 |
| 2010/0029980 | A1 | 2/2010 | Johnston et al. | WO | 2009063176 A1 | 5/2009 |
| 2010/0029993 | A1 | 2/2010 | Johnston et al. | WO | WO 2009/086839 | 7/2009 |
| 2010/0029995 | A1 | 2/2010 | Johnston | WO | WO 2009/105860 | 9/2009 |
| 2010/0029996 | A1 | 2/2010 | Danjo et al. | WO | 2010014151 A2 | 2/2010 |
| 2010/0030001 | A1 | 2/2010 | Chen et al. | WO | WO 2010/014145 | 2/2010 |
| 2010/0030002 | A1 | 2/2010 | Johnston et al. | WO | WO 2010/014148 | 2/2010 |
| 2010/0069514 | A1 | 3/2010 | Gracey et al. | WO | WO 2010/014152 | 2/2010 |
| 2010/0113843 | A1 | 5/2010 | Lee | WO | WO 2010/014153 | 2/2010 |
| 2010/0121114 | A1 | 5/2010 | Weiner et al. | WO | 2010056299 | 5/2010 |
| 2010/0125148 | A1 | 5/2010 | Johnston et al. | WO | WO 2010/055285 | 5/2010 |
| 2010/0168466 | A1 | 7/2010 | Johnston et al. | WO | WO 2011/053365 | 5/2011 |
| 2010/0168493 | A1 | 7/2010 | LePeltier | WO | WO 2011/053367 A1 | 5/2011 |
| 2010/0185021 | A1 | 7/2010 | Ross et al. | | | |
| 2010/0196789 | A1 | 8/2010 | Fisher | | | |
| 2010/0197485 | A1 | 8/2010 | Johnston et al. | | | |
| 2010/0197959 | A1 | 8/2010 | Johnston et al. | | | |
| 2010/0197985 | A1 | 8/2010 | Johnston et al. | | | |
| 2010/0249479 | A1 | 9/2010 | Berg-Slot | | | |
| 2011/0004033 | A1 | 1/2011 | Johnston et al. | | | |
| 2011/0046421 | A1 | 2/2011 | Daniel et al. | | | |
| 2011/0065572 | A1 | 3/2011 | Olken et al. | | | |
| 2011/0071312 | A1 | 3/2011 | Johnston et al. | | | |
| 2011/0082322 | A1 | 4/2011 | Jevtic et al. | | | |
| 2011/0282109 | A1 | 11/2011 | Johnston et al. | | | |
| 2012/0238785 | A1 | 9/2012 | Zhou et al. | | | |
| 2012/0253085 | A1 | 10/2012 | Johnston et al. | | | |

FOREIGN PATENT DOCUMENTS

| | | |
|---|---|---|
| CN | 102229520 | 11/2011 |
| EP | 0175558 A1 | 3/1986 |
| EP | 0 192 587 A1 | 8/1986 |
| EP | 0192587 | 8/1986 |
| EP | 0330853 A2 | 9/1989 |
| EP | 0372847 A2 | 12/1989 |
| EP | 0372847 | 6/1990 |
| EP | 0400904 | 12/1990 |
| EP | 0407038 | 1/1991 |
| EP | 0408528 | 1/1991 |
| EP | 0198682 B1 | 3/1991 |
| EP | 0285420 B1 | 5/1991 |
| EP | 0456647 | 11/1991 |
| EP | 0539274 | 4/1993 |
| EP | 0285786 B1 | 5/1993 |
| EP | 0 653 242 A1 | 5/1995 |
| EP | 0167300 | 11/1998 |
| EP | 0953560 | 11/1999 |
| EP | 0990638 | 4/2000 |
| EP | 0104197 | 2/2001 |
| EP | 1277826 | 2/2001 |
| EP | 0137749 | 6/2001 |
| EP | 2186787 | 6/2001 |
| EP | 1262234 | 12/2002 |
| EP | 2060553 A1 | 5/2009 |
| EP | 2060555 A1 | 5/2009 |
| EP | 2072487 | 6/2009 |
| EP | 2072488 | 6/2009 |
| EP | 2072489 | 6/2009 |
| EP | 2072492 | 6/2009 |
| EP | 2 186 787 A1 | 5/2010 |
| GB | 1168785 | 10/1969 |

OTHER PUBLICATIONS

Ammari, et al. "Selective hydrogenation of crotonaldehyde on Pt/ZnCl2/SiO2 catalysts," J. Catal. (2005), 235, p. 1-9.

Consonni, et al. "High Performances of Pt/ZnO Catalysts in Selective Hydrogenation of Crotonaldehyde," J. Catal. (1999), 188, p. 165-175.

Nitta, et al. "Selective hydrogenation of αβ-unsaturated aldehydes on cobalt—silica catalysts obtained from cobalt chrysotile," Applied Catal. (1989), 56, p. 9-22.

T. Yokoyama et al., "Carboxylic Acids and Derivatives", Fine Chemicals through Heterogenous Catalysis, pp. 370-379.

International Search Report and Written Opinion for PCT/US2010/054136 mailed May 25, 2011 (19 pages).

English abstract for JP 11-147845.

English abstract for EP0456647.

English abstract for CN1230458.

English abstract for JP6-116182.

Jingfa D et al: "Acidic properties of ZSM-5 zeolite and conversion of ethanol to diethyl ether" Applied Catalysis, Amsterdam, NL, vol. 41, Jan. 1, 1988, pp. 13-22, XP 009144884 (10 pages).

Nefedov and I V Mishin B K: "Synthesis of diethyl ether in presence of zeolite catalysts", Russian Chemical Bulletin, Springer New York LLC, US; RU, vol. 28, Jan. 1, 1979, pp. 183-186, XP009144865 (4 Pages).

Written Opinion for PCT/US2010/054136 dated Mar. 16, 2012.

International Search Report for PCT/US2011/023272 dated Aug. 11, 2011.

International Search Report and Written Opinion for PCT/US2011/023269 mailed Aug. 5, 2011.

International Search Report and Written Opinion for PCT/US2010/054132 mailed Feb. 28, 2011.

Written Opinion for PCT/US2010/054132 mailed Nov. 29, 2011.

International Preliminary Report on Patentability for PCT/US2010/054132 mailed Feb. 1, 2012.

International Search Report and Written Opinion for PCT/US2010/054134 mailed Feb. 28, 2011.

International Search Report and Written Opinion for PCT/US2010/022950 mailed Sep. 7, 2011.

U. S. Office Action mailed Mar. 13, 2012 in U.S. Appl. No. 12/852,305.

U. S. Office Action mailed Mar. 12, 2012 in U.S. Appl. No. 13/267,146.

U. S. Office Action mailed Mar. 12, 2012 in U.S. Appl. No. 12/852,227.

International Preliminary Report on Patentability mailed May 18, 2012 in corresponding International Application No. PCT/US2010/054136.

International Written Opinion mailed May 8, 2012 in corresponding International Application No. PCT/US2011/023269.

Brunauer Emmett and Teller, J. Am. Chem. Soc. 60, 309 (1938).

Proc. Roy Soc. A314, pp. 473-498 (1970).

Invitation to Pay Additional Fees and Partial Search Report for PCT/US2010/054136 mailed Feb. 28, 2011 (7 pages).

Pestman et al., The formation of ketones and aldehydes from carboxylic acids, structure-activity relationship for two competitive reactions, Journal of Molecular Catalysis A: Chemical 103 Jun. 14, 1995, 175-180.

English language abstract for JP6116182A.

International Search Report and Written Opinion for PCT/US2010/022947 mailed Jun. 7, 2010.

International Search Report and Written Opinion for PCT/US2010/022949 mailed Jun. 7, 2010.

International Search Report and Written Opinion for PCT/US2010/022950 mailed Jun. 15, 2010.

International Search Report and Written Opinion for PCT/US2010/022953 mailed Jun. 7, 2010.

International Search Report and Written Opinion mailed on May 22, 2012 in corresponding International Application No. PCT/US2012/031207.

Minglin Xiang et al., "XPS study of potassium-promoted molybdenum carbides for mixed alcohols synthesis via CO hydrogenation", Journal of Natural Gas Chemistry, vol. 19, 2010, pp. 151-155.

Zheng, et al., (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al., (2000). Hydrogenation of carbonylic compounds on Pt/SiO2 catalysts modified with SnBu4, Studies in Surface Science and Catalysis, 130, 2063-2068.

Rachmady, The formation of ketones and aldehydes from carboxylic acids, structure-activity relationship for two competitive reactions, Journal of Molecular Catalysis A: Chemical 103 Jun. 14, 1995, 175-180.

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

International Search Report and Written Opinion for PCT/US2009/004197 mailed Mar. 24, 2010 (14 pages).

International Search Report and Written Opinion for PCT/US2009/004195 mailed Mar. 26, 2010 (12 pages).

Written Opinion mailed Jan. 24, 2012 in corresponding International Application No. PCT/US2010/022950.

U.S. Office Action mailed Oct. 24, 2012 in co-pending U.S. Appl. No. 13/179,955.

U.S. Office Action mailed Oct. 15, 2012 in co-pending U.S. Appl. No. 12/850,414.

U.S. Office Action mailed Dec. 12, 2012 in co-pending U.S. Appl. No. 12/698,947.

U.S. Office Action mailed Nov. 29, 2012 in co-pending U.S. Appl. No. 12/699,024.

U.S. Office Action mailed Dec. 18, 2012 in co-pending U.S. Appl. No. 12/698,968.

Invitation to Pay Additional Fees mailed Nov. 30, 2012 in corresponding International Application No. PCT/US2012/052510.

International Preliminary Report on Patentability mailed Feb. 14, 2012 in corresponding International Application No. PCT/US2010/022950.

International Preliminary Report on Patentability mailed Oct. 8, 2010 in corresponding International Application No. PCT/US2009/004197.

DuPont, "Innovation", vol. 4, No. 3, Spring 1973.

D. Domine and J. Quobex, Mol. Sieves Pap. Conf., (1967), 78, Soc. Chem. Ind. London.

DePuy and King, Chern. Rev., 60, 431-445 (1960).

US 8,546,622 B2

PROCESS FOR MAKING ETHANOL FROM ACETIC ACID USING ACIDIC CATALYSTS

CROSS REFERENCE TO RELATED APPLICATIONS

This is a continuation-in-part application of U.S. application Ser. No. 12/699,024, filed Feb. 2, 2010; U.S. application Ser. No. 12/698,947, filed Feb. 2, 2010; U.S. application Ser. No. 12/588,727, filed Oct. 26, 2009; and U.S. application Ser. No. 12/221,141, filed Jul. 31, 2008. This application also is a continuation-in-part of U.S. application Ser. No. 12/852,227, filed Aug. 6, 2010, which claims priority to U.S. Provisional App. No. 61/300,815, filed Feb. 2, 2010, and U.S. Provisional App. No. 61/332,696, filed May 7, 2010. This application also is a continuation-in-part of U.S. application Ser. No. 12/852,269, filed Aug. 6, 2010, which claims priority to U.S. Provisional App. No. 61/300,815, filed Feb. 2, 2010 and U.S. Provisional App. No. 61/332,699, filed May 7, 2010. The entireties of these applications are incorporated herein by reference.

FIELD OF THE INVENTION

The present invention relates generally to processes for producing ethanol and, in particular, to processes for producing ethanol from the hydrogenation of acetic acid using acidic catalysts.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol for fuels or consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities and byproducts limit the production and recovery of ethanol from such reaction mixtures. For example, during hydrogenation, esters are produced that together with ethanol and/or water, form azeotropes, which are difficult to separate. In addition, when conversion is incomplete, unreacted acid remains in the crude ethanol product, which must be removed to recover ethanol.

Thus, the need remains for improved processes for producing ethanol via alkanoic acid reduction, which yield crude ethanol products containing fewer impurities and byproducts.

SUMMARY OF THE INVENTION

In a first embodiment, the present invention is directed to a process for producing ethanol, comprising hydrogenating acetic acid in the presence of a catalyst to form ethanol, wherein the hydrogenation has a selectivity to ethanol of at least 65% wherein the catalyst comprises a first metal on an acidic support selected from the group consisting of (i) an acidic support material selected from the group consisting of iron oxide, alumina, silica/aluminas, titania, zirconia, and mixtures thereof, and (ii) a support material modified with an acidic modifier.

In a second embodiment, the present invention is directed to a process for producing ethanol, comprising hydrogenating acetic acid in the presence of a first catalyst to form an intermediate product comprising ethanol and unreacted acetic acid; and hydrogenating the unreacted acetic acid in the present of a second catalyst to form ethanol. The first catalyst comprising a catalyst comprising one or more metals, a siliceous support, and at least one basic support modifier. The second catalyst comprises a first metal on an acidic support selected from the group consisting of (i) an acidic support material selected from the group consisting of iron oxide, alumina, silica/aluminas, titania, zirconia, and mixtures thereof, and (ii) a support material modified with an acidic modifier.

In a third embodiment, the present invention is directed to a process for producing ethanol, comprising hydrogenating acetic acid in the presence of a first catalyst and a second catalyst in a reactor to form ethanol. The first catalyst may be in a first reactor region and the second catalyst may be in a second reactor region, that is separated from the first reactor region. The first catalyst comprising a catalyst comprising one or more metals, a siliceous support, and at least one basic support modifier. The second catalyst comprises a first metal on an acidic support selected from the group consisting of: (i) an acidic support material selected from the group consisting of iron oxide, alumina, silica/aluminas, titania, zirconia, and mixtures thereof, and (ii) a support material modified with an acidic modifier.

In a fourth embodiment, the present invention is directed to a process for recovering ethanol, comprising hydrogenating an acetic acid feed stream in a reactor comprising a catalyst to form a crude ethanol product. The catalyst comprises a first metal on an acidic support selected from the group consisting of (i) an acidic support material selected from the group consisting of iron oxide, alumina, silica/aluminas, titania, zirconia, and mixtures thereof, and (ii) a support material modified with an acidic modifier. The process further comprises separating at least a portion of the crude ethanol product in a first column into a first distillate comprising ethanol, water and ethyl acetate, and a first residue comprising acetic acid; separating at least a portion of the first distillate in a second column into a second distillate comprising ethyl acetate and a second residue comprising ethanol and water; returning at least a portion of the second distillate to the reactor; and separating at least a portion of the second residue in a third column into a third distillate comprising ethanol and a third residue comprising water.

The acidic modifier used in embodiments of the present invention preferably is selected from the group consisting of oxides of Group IVB metals, oxides of Group VB metals, oxides of Group VIB metals, oxides of Group VIIB metals, oxides of Group VIIIB metals, aluminum oxides, and mixtures thereof.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
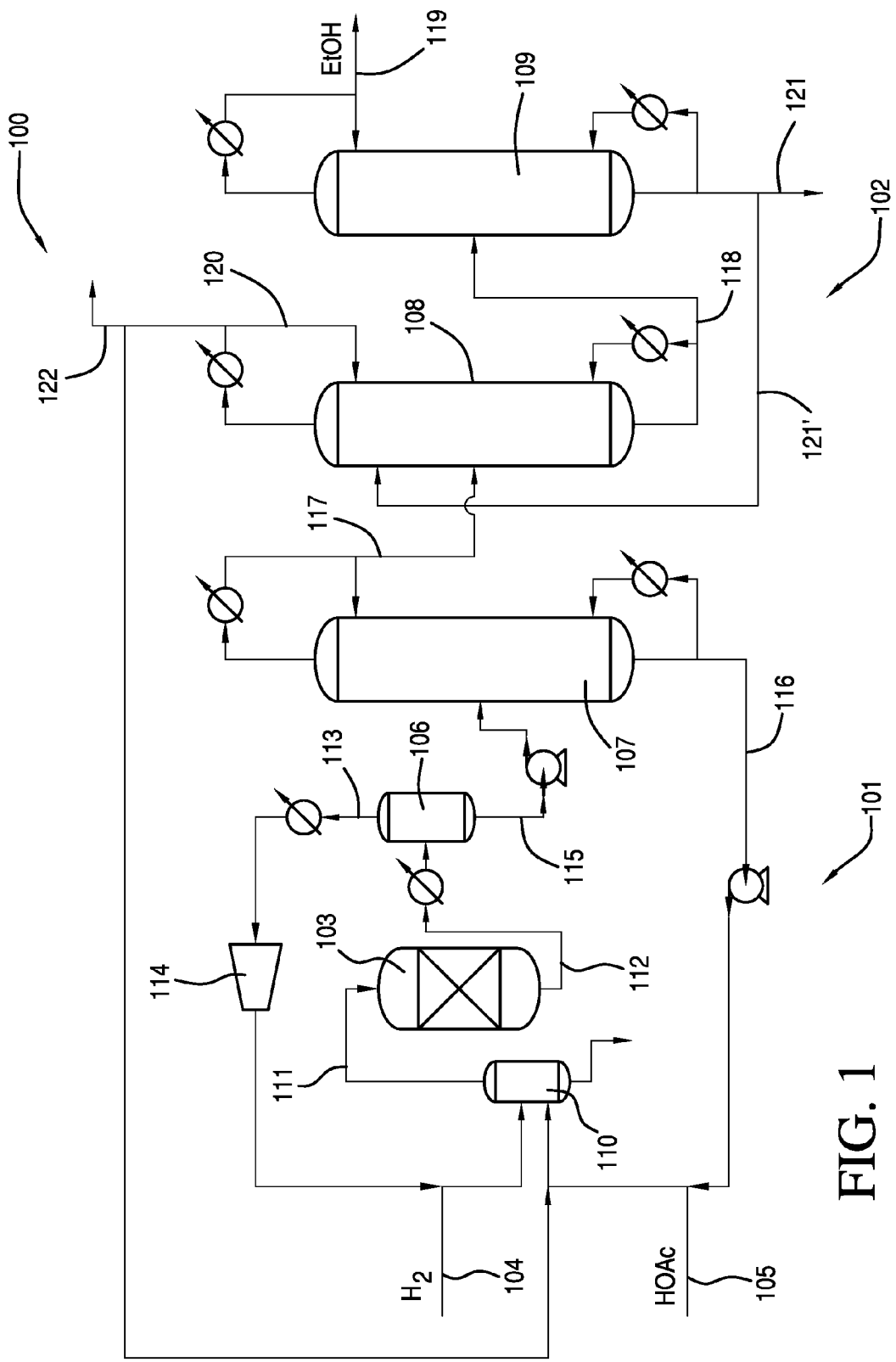
FIG. 1 is a schematic diagram of a hydrogenation system in accordance with one embodiment of the present invention.

The present invention relates to processes for producing ethanol and to processes for recovering ethanol from a crude ethanol product. The crude acetic acid product, in one embodiment, is produced by a hydrogenation process comprising hydrogenating acetic acid in the presence of an acidic catalyst. In one embodiment, the acidic catalyst comprises a first metal on an acidic support. In one embodiment, the acidic catalyst comprises a first metal on a support and an acidic support modifier.

During hydrogenation of acetic acid, there are other side reactions that produce impurities and byproducts. One principal side reaction is an equilibrium reaction between acetic acid/ethanol and ethyl acetate/water also occurs. The two main reactions are:

HOAc+2H$_2$⇌EtOH+H$_2$O        Reaction 1

HOAc+EtOH⇌EtOAc+H$_2$O        Reaction 2

Reaction 2 is reversible and the equilibrium constant, Keq is given by Equation 1:

$$K_{eq} = \frac{k^2}{k^{-2}} = \frac{[EtOAc][H_2O]}{[HOAc][EtOH]} \quad \text{Equation 1}$$

Generally, to produce ethanol the reaction conditions favor the first reaction over the second reaction, which consumes ethanol and increases the ethyl acetate byproducts in the crude ethanol product. In U.S. Pub. No. 2010/0197985, the entirety of which is incorporated herein by reference, the first reaction is favored and is promoted by the use of a catalyst comprising a basic modifier.

In some embodiments, the present invention uses an acidic catalyst, which preferably comprises a first metal on an acidic support. Without being bound by theory, it is believed that the second reaction is promoted in the presence of acid. Also in the vapor phase, $K_{eq}$ is believed to decrease at higher temperatures. In embodiments of the present invention, $K_{eq}$ may be less than 20, e.g., less than 15 or less than 12. Preferably, $K_{eq}$ may be less than 6, e.g., less than 4 or less than 3. As such, the acidic catalyst increases forward and reverse reaction rates for the equilibrium reaction. In embodiments where $K_{eq}>1$, and under reaction conditions that favor high conversions of acetic acid, the selectivity to ethanol is surprisingly and unexpectedly high. The productivity of ethanol also increases at high conversions. Increasing conversion and selectivity to ethanol advantageously reduce the amount of byproducts in the crude ethanol product and, as a result, may improve the efficiency of recovering ethanol.

For purposes of the present invention, the term "conversion" refers to the amount of acetic acid in the feed that is converted to a compound other than acetic acid. Conversion is expressed as a mole percentage based on acetic acid in the feed. Selectivity is expressed as a mole percent based on converted acetic acid. It should be understood that each compound converted from acetic acid has an independent selectivity and that selectivity is independent from conversion. For example, if 50 mole % of the converted acetic acid is converted to ethanol, the ethanol selectivity is 50%.

At low conversion of acetic acid, e.g. less than about 50%, an acidic catalyst tends to show increased selectivity to ethyl acetate over ethanol. Thus, in some embodiments of the present invention, to produce ethanol, the conversion of acetic acid is preferably greater than 70%, e.g., greater than 80%, greater than 90% or greater than 95%.

In the inventive processes, the selectivity to ethanol is preferably at least 65%, e.g., at least 70%, at least 80%, at least 85%, or at least 90%. At lower conversions of acetic acid, around 70%, the selectivity to ethanol may be approximately 30% to 40%. Preferably, as the acetic acid conversion increases the selectivity to the ethanol also increases. In addition, the selectivity to ethyl acetate may be low, e.g., less than 35%, less than 30%, less than 10%, or less than 5%. Preferably, the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not readily detectable in the crude ethanol product. Formation of alkanes may be low. Ideally less than 2% of the acetic acid passed over the catalyst is converted to alkanes, e.g., less than 1%, or less than 0.5%.

Embodiments of the present invention provide for increased productivity of ethanol at high conversions of acetic acid. When acetic acid conversion is preferably greater than 90%, the selectivity to ethanol preferably is at least 70%. Selectivity may continue to increase as conversion of acetic acid increases.

The term "productivity," as used herein, refers to the grams of a specified product, e.g., ethanol, formed during the hydrogenation per kilogram of catalyst used per hour. A productivity of at least 200 grams of ethanol per kilogram catalyst per hour is preferred, e.g., at least 400 or at least 600. In terms of ranges, the productivity preferably is from 200 to 3,000 grams of ethanol per kilogram catalyst per hour, e.g., from 400 to 2,500 or from 600 to 2,000.

Embodiments of the present invention provide for increase productivity at high conversion of acetic acid. At 70% or greater acetic acid conversion the productivity of ethanol is at least 350 grams of ethanol per kilogram catalyst per hour. Productivity may continue to increase as conversion of acetic acid increases.

The hydrogenation of acetic acid to form ethanol and water is conducted in the present of an acidic catalyst. In one embodiment, hydrogenation catalysts comprises a first metal on an acidic support and optionally one or more of a second metal, a third metal or additional metals. The first and optional second and third metals may be selected from Group IB, IIB, IIIB, IVB, VB, VIIB, VIIB, VIII transitional metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Pub. Nos. 2010/0029995 and 2010/0197985, the entireties of which are incorporated herein by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. In one embodiment, the metal loading of the acidic catalyst may be reduced. This may advantageously decrease the costs associated with catalyst having higher metal loadings. Thus, in embodiments having reduced metal loadings, the first metal may be present in amounts from 0.1 to 1.7 wt. % and the second metal may be present in amounts from 0.1 to 1.3 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1. In one embodiment, to favor selectivity to ethanol where the catalyst comprises platinum and tin, the Pt/Sn molar ratio preferably is from 0.4:0.6 to 0.6:0.4, e.g., from 0.45:0.55 to 0.55:0.45 or about 1:1. In another embodiment, to favor selectivity to ethanol in embodiments where the catalyst comprises rhenium and palladium, the Re/Pd molar ratio preferably is from 0.6:0.4 to 0.85:0.15, e.g., from 0.7:0.3 to 0.85:0.15, or a molar ratio of about 0.75:0.25.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 and 4 wt. %, e.g., from 0.1 to 3 wt. %, or from 0.1 to 2 wt. %.

In addition to the one or more metals, the inventive acidic catalysts, in some embodiments, further comprise an acidic support material or modified support material. A modified support material comprises a support material and an acidic support modifier. An acidic support modified adjusts the acidity of the support material. The total weight of the support material or modified support material, based on the total weight of the catalyst, preferably is from 75 wt. % to 99.9 wt. %, e.g., from 78 wt. % to 97 wt. %, or from 80 wt. % to 95 wt. %. In embodiments that use a modified support material, the catalyst may comprise the support modifier in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred support materials include are selected from the group consisting of silica, silica/alumina, calcium metasilicate, pyrogenic silica, high purity silica, carbon, iron oxide, alumina, silica/aluminas, titania, zirconia, and mixtures thereof. In one preferred embodiment, an acidic support material may be used for the catalyst. Acidic support materials are selected from the group consisting of iron oxide, alumina, silica/aluminas, titania, zirconia, and mixtures thereof.

In the production of ethanol, the catalyst support material may be modified with a support modifier. Preferably, the catalyst support material that are basic or neutral, such as silica, metasilicate, pyrogenic silica, high purity silica, carbon, or mixtures thereof are modified with an acidic support modifier. Acidic support materials may also be modified with an acidic support modifier. In some embodiments, the acidic support modifier adjusts the support material by increasing the number or availability of acid sites. The acidic sites promote the kinetic rate of the esterification equilibrium. Preferably, the support modifier is an acidic modifier that has a low volatility or no volatility. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $CO_2O_3$, $Bi_2O_3$.

In one preferred aspect of the present invention, the acidic catalyst comprises:
(i) a first metal comprising a Group VIII metal,
(ii) a second metal comprising copper, molybdenum, tin, chromium, iron, cobalt, vanadium, tungsten, palladium, platinum, lanthanum, cerium, manganese, ruthenium, rhenium, gold, and nickel, and
(iii) an acidic support that comprises an acidic support material selected from the group consisting of iron oxide, alumina, silica/aluminas, titania, zirconia, and mixtures thereof.

The acidic support may further comprise an acidic support modifier.

In another preferred aspect of the present invention, the acidic catalyst comprises:
(i) a first metal comprising a Group VIII metal,
(ii) a second metal comprising copper, molybdenum, tin, chromium, iron, cobalt, vanadium, tungsten, palladium, platinum, lanthanum, cerium, manganese, ruthenium, rhenium, gold, and nickel, and
(iii) an acidic support that comprises a support material and an acidic support modifier.

A preferred silica support material is SS61138 High Surface Area (HSA) Silica Catalyst Carrier from Saint-Gobain N or Pro. The Saint-Gobain N or Pro SS61138 silica contains approximately 95 wt. % high surface area silica; a surface area of about 250 m$^2$/g; a median pore diameter of about 12 nm; an average pore volume of about 1.0 cm$^3$/g as measured by mercury intrusion porosimetry and a packing density of about 0.352 g/cm$^3$ (22 lb/ft$^3$).

A preferred silica/alumina support material is KA-160 (Sud Chemie) silica spheres having a nominal diameter of about 5 mm, a density of about 0.562 g/ml, in absorptivity of about 0.583 g H$_2$O/g support, a surface area of about 160 to 175 m$^2$/g, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744, U.S. Pub. Nos. 2010/0029995, and 2010/0197985, the entireties of which are incorporated herein by reference.

Embodiments of the invention may include a variety of reactor configurations using a fixed bed reactor or a fluidized bed reactor, as one of skill in the art will readily appreciate. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 50,000 e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, such a process can also be used to make hydrogen which may be utilized in connection with this invention.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the disclosure of which is incorporated herein by reference. Optionally, the production of ethanol may be integrated with such methanol carbonylation processes.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas as well as U.S. Pat. No. 6,685,754, the disclosures of which are incorporated herein by reference.

In one optional embodiment, the acetic acid fed to the hydrogenation reaction may also comprise other carboxylic acids and anhydrides, as well as acetaldehyde and acetone.

Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the present of carboxylic acids, such as propanoic acid or its anhydride, may be beneficial in producing propanol.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor by passing hydrogen and/or recycle gas through the acetic acid at a temperature at or below 125° C., followed by heating of the combined gaseous stream to the reactor inlet temperature.

In various embodiments, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some exemplary embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 35 wt. %, e.g., from 10 to 30 wt. % or from 10 to 26 wt. %. Ethyl acetate may also be produced during the hydrogenation of acetic acid or through side reactions and may be present, for example, in amounts ranging from 0 to 20 wt. %, e.g., from 0 to 15 wt. %, from 1 to 12 wt. % or from 3 to 10 wt. %. Acetaldehyde may also be produced through side reactions and may be present, for example, in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, other components may be present in an amount from 0.1 to 10 wt. %, e.g., from 0.1 to 6 wt. %, or from 0.1 to 4 wt. %. Exemplary embodiments of crude ethanol compositional ranges are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 70 | 15 to 70 | 25 to 70 |
| Acetic Acid | 0 to 80 | 0 to 50 | 0 to 25 | 0 to 10 |
| Water | 5 to 35 | 5 to 30 | 10 to 30 | 10 to 26 |
| Ethyl Acetate | 0 to 30 | 0 to 20 | 0 to 15 | 0 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

FIG. 1 shows a hydrogenation system 100 suitable for the hydrogenation of acetic acid and separating ethanol from the crude reaction mixture according to one embodiment of the invention. System 100 comprises reaction zone 101 and distillation zone 102. Reaction zone 101 comprises reactor 103, hydrogen feed line 104 and acetic acid feed line 105. Distillation zone 102 comprises flasher 106, first column 107, second column 108, and third column 109. Hydrogen and acetic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1, and may be recycled thereto. In addition, although FIG. 1 shows line 111 being directed to the top of reactor 103, line 111 may be directed to the side, upper portion, or bottom of reactor 103. Further modifications and additional components to reaction zone 101 are described below in FIGS. 2A and 2B.

Reactor 103 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product stream is withdrawn, preferably continuously, from reactor 103 via line 112. The crude ethanol product stream may be condensed and fed to flasher 106, which, in turn, provides a vapor stream and a liquid stream. The flasher 106 in one embodiment preferably operates at a temperature of from 50° C. to 500° C., e.g., from 70° C. to 400° C. or from 100° C. to 350° C. In one embodiment, the pressure of flasher 106 preferably is from 50 KPa to 2000 KPa, e.g., from 75 KPa to 1500 KPa or from 100 to 1000 KPa. In one preferred embodiment the temperature and pressure of the flasher is similar to the temperature and pressure of the reactor 103.

The vapor stream exiting the flasher 106 may comprise hydrogen and hydrocarbons, which may be purged and/or returned to reaction zone 101 via line 113. As shown in FIG.

1, the returned portion of the vapor stream passes through compressor 114 and is combined with the hydrogen feed and co-fed to vaporizer 110.

The liquid from flasher 106 is withdrawn and pumped as a feed composition via line 115 to the side of first column 107, also referred to as the acid separation column. The contents of line 115 typically will be substantially similar to the product obtained directly from the reactor, and may, in fact, also be characterized as a crude ethanol product. However, the feed composition in line 115 preferably has substantially no hydrogen, carbon dioxide, methane or ethane, which are removed by flasher 106. Exemplary components of liquid in line 115 are provided in Table 2. It should be understood that liquid line 115 may contain other components, not listed, such as components in the feed.

TABLE 2

FEED COMPOSITION

|  | Conc. (wt. %) | Conc. (wt. %) | Conc. (wt. %) |
|---|---|---|---|
| Ethanol | 5 to 70 | 10 to 70 | 25 to 70 |
| Acetic Acid | <80 | 0 to 50 | 0 to 10 |
| Water | 5 to 35 | 5 to 30 | 10 to 26 |
| Ethyl Acetate | <30 | 0.001 to 20 | 1 to 10 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 115, may comprise propanol, e.g., isopropanol and/or n-propanol, in an amount from 0.001 to 0.1 wt. %, from 0.001 to 0.05 wt. % or from 0.001 to 0.03 wt. %. It should be understood that these other components may be carried through in any of the distillate or residue streams described herein and will not be further described herein, unless indicated otherwise.

In one embodiment, the conversion of acetic acid may be greater than 95%, and the crude ethanol product in line 115 may contain less than 5 wt. % acetic acid. In such embodiments, the acid separation column 107 may be skipped and line 115 may be introduced directly to second column 108, also referred to herein as a light ends column.

In the embodiment shown in FIG. 1A, line 115 is introduced in the lower part of first column 107, e.g., lower half or lower third. In first column 107, unreacted acetic acid, a portion of the water, and other heavy components, if present, are removed from the composition in line 115 and are withdrawn, preferably continuously, as residue. Some or all of the residue may be returned and/or recycled back to reaction zone 101 via line 116. First column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

Any of columns 107, 108 or 109 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIG. 1. As shown in FIG. 1, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIG. 1, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependent on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 105° C. to 117° C. or from 110° C. to 115° C. The temperature of the distillate exiting in line 117 from column 107 preferably is from 70° C. to 110° C., e.g., from 75° C. to 95° C. or from 80° C. to 90° C. In other embodiments, the pressure of first column 107 may range from 0.1 KPa to 510 KPa, e.g., from 1 KPa to 475 KPa or from 1 KPa to 375 KPa. Exemplary components of the distillate and residue compositions for first column 107 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

|  | Conc. (wt. %) | Conc. (wt. %) | Conc. (wt. %) |
|---|---|---|---|
| Distillate |  |  |  |
| Ethanol | 5 to 75 | 10 to 70 | 25 to 70 |
| Water | 10 to 40 | 15 to 35 | 20 to 35 |
| Acetic Acid | <2 | 0.001 to 0.5 | 0.01 to 0.2 |
| Ethyl Acetate | <60 | 0 to 20 | 0 to 10 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude ethanol product exiting reactor 103 in line 112 may comprise ethanol, acetic acid (unconverted), ethyl acetate, and water. After exiting reactor 103, a non-catalyzed equilibrium reaction may occur between the components contained in the crude ethanol product until it is added to flasher 106 and/or first column 107. This equilibrium reaction tends to drive the crude ethanol product to an equilibrium between ethanol/acetic acid and ethyl acetate/water, as shown below (Reaction 2).

$$EtOH + HOAc \rightleftharpoons EtOAc + H_2O \qquad \text{Reaction 2}$$

In the event the crude ethanol product is temporarily stored, e.g., in a holding tank, prior to being directed to distillation zone 102, extended residence times may be encountered. Generally, the longer the residence time between reaction zone 101 and distillation zone 102, the greater the formation of ethyl acetate. For example, when the residence time between reaction zone 101 and distillation zone 102 is greater than 5 days, significantly more ethyl acetate may form at the expense of ethanol. Thus, shorter residence times between reaction zone 101 and distillation zone 102 are generally preferred in order to maximize the amount of ethanol formed. In one embodiment, a holding tank (not shown), is included between the reaction zone 101 and distillation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude ethanol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and distillation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in line 115 increase from 4° C. to 21° C., the rate of ethyl acetate formation may increase from about 0.01 wt. % per hour to about 0.005 wt. % per hour. Thus, in one embodiment, the temperature of liquid components in line 115 or in the optional holding tank is maintained at a temperature less than 21° C., e.g., less than 4° C. or less than −10° C.

In addition, it has now been discovered that the above-described equilibrium reaction may also favor ethanol formation in the top region of first column 107.

The distillate, e.g., overhead stream, of column 107 optionally is condensed and refluxed as shown in FIG. 1, preferably, at a reflux ratio of 1:5 to 10:1. The distillate in line 117 preferably comprises ethanol, ethyl acetate, and water, along with other impurities, which may be difficult to separate due to the formation of binary and tertiary azeotropes.

The first distillate in line 117 is introduced to the second column 108, also referred to as the "light ends column," preferably in the middle part of column 108, e.g., middle half or middle third. As one example, when a 25 tray column is utilized in a column without water extraction, line 117 is introduced at tray 17. In one embodiment, the second column 108 may be an extractive distillation column. In such embodiments, an extraction agent, such as water, may be added to second column 108. If the extraction agent comprises water, it may be obtained from an external source or from an internal return/recycle line from one or more of the other columns, such as via optional line 121'.

Second column 108 may be a tray column or packed column. In one embodiment, second column 108 is a tray column having from 5 to 70 trays, e.g., from 15 to 50 trays or from 20 to 45 trays.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 120 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 KPa to 510 KPa, e.g., from 1 KPa to 475 KPa or from 1 KPa to 375 KPa. Exemplary components for the distillate and residue compositions for second column 108 are provided in Table 4 below. It should be understood that the distillate and residue may also contain other components, not listed, such as components in the feed.

TABLE 4

SECOND COLUMN

|  | Conc. (wt. %) | Conc. (wt. %) | Conc. (wt. %) |
|---|---|---|---|
| Distillate |  |  |  |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |

TABLE 4-continued

SECOND COLUMN

|  | Conc. (wt. %) | Conc. (wt. %) | Conc. (wt. %) |
|---|---|---|---|
| Ethanol | <30 | 0.001 to 15 | 0.01 to 5 |
| Acetal | <5 | 0.001 to 2 | 0.01 to 1 |
| Residue | | | |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate approaches zero.

As shown, the second residue from the bottom of second column 108, which comprises ethanol and water, is fed via line 118 to third column 109, also referred to as the "product column." More preferably, the second residue in line 118 is introduced in the lower part of third column 109, e.g., lower half or lower third. Third column 109 recovers ethanol, which preferably is substantially pure other than the azeotropic water content, as the distillate in line 119. The distillate of third column 109 preferably is refluxed as shown in FIG. 1A, for example, at a reflux ratio of from 1:10 to 10:1, e.g., from 1:3 to 3:1 or from 1:2 to 2:1. The third residue in line 121, which preferably comprises primarily water, preferably is removed from the system 100 or may be partially returned to any portion of the system 100. Third column 109 is preferably a tray column as described above and preferably operates at atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C., when the column is operated at atmospheric pressure. Exemplary components of the distillate and residue compositions for third column 109 are provided in Table 5 below. It should be understood that the distillate and residue may also contain other components, not listed, such as components in the feed.

TABLE 5

THIRD COLUMN

|  | Conc. (wt. %) | Conc. (wt. %) | Conc. (wt. %) |
|---|---|---|---|
| Distillate | | | |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue | | | |
| Water | 75 to 100 | 80 to 100 | 90 to 100 |
| Ethanol | <0.8 | 0.001 to 0.5 | 0.005 to 0.05 |

TABLE 5-continued

THIRD COLUMN

|  | Conc. (wt. %) | Conc. (wt. %) | Conc. (wt. %) |
|---|---|---|---|
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 107, 108 and/or 109 in the system 100. Preferably at least one side stream is used to remove impurities from the third column 109. The impurities may be purged and/or retained within the system 100.

The third distillate in line 119 may be further purified to form an anhydrous ethanol product stream, i.e., "finished anhydrous ethanol," using one or more additional separation systems, such as, for example, distillation columns (e.g., a finishing column) or molecular sieves.

Returning to second column 108, the distillate in line 120 preferably is refluxed as shown in FIG. 1, for example, at a reflux ratio of from 1:10 to 10:1, e.g., from 1:5 to 5:1 or from 1:3 to 3:1. In one embodiment, all or a portion of the distillate from second column 108 may be recycled to reaction zone 101 via line 120. As shown in FIG. 1, all or a portion the distillate may be recycled to reactor 103, as shown by line 120, and may be co-fed with the acetic acid feed line 105. In one embodiment, ethyl acetate in line 120 does not build up in the reaction zone 101 and/or distillation zone 102 due to the presence of the catalyst comprising an acidic support. Due to the increase in kinetics of the equilibrium reaction, embodiments of the present invention are able to process ethyl acetate in the feed and/or recycle stream as well. Thus, because of the increased kinetics, the recycled ethyl acetate in line 120 may be converted to ethanol, or the generated ethyl acetate may be equal to the converted ethyl acetate so there will be certain steady state achieved relatively fast and recycled ethyl acetate concentration will remain constant; without building up in the recycle loop. A portion of the distillate from second column 108 may be purged via line 122. Optionally, the second distillate in line 120 may be further purified to remove impurities, such as acetaldehyde, using one or more additional columns (not shown) before being returned to the reaction zone, as described in co-pending U.S. application Ser. No. 12/852, 269, the entirety of which is hereby incorporated by reference.

Figure 2A:
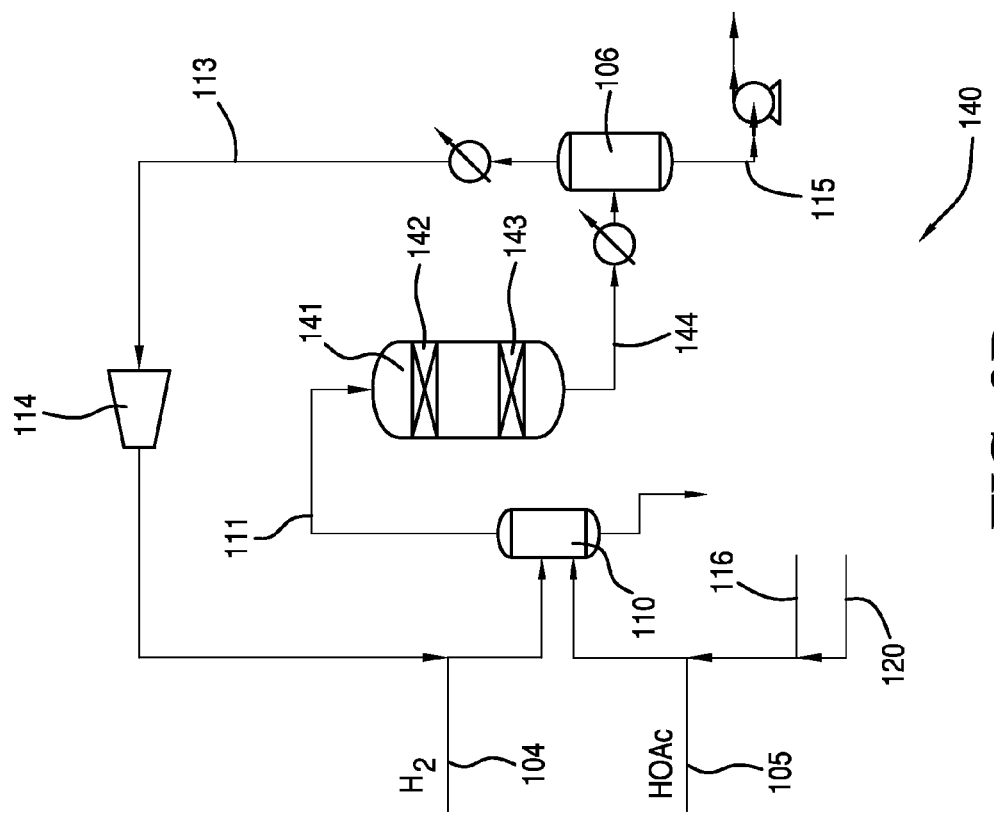
FIG. 2A is a schematic diagram of a reaction zone having dual reactors in accordance with one embodiment of the present invention.
Figure 2B:
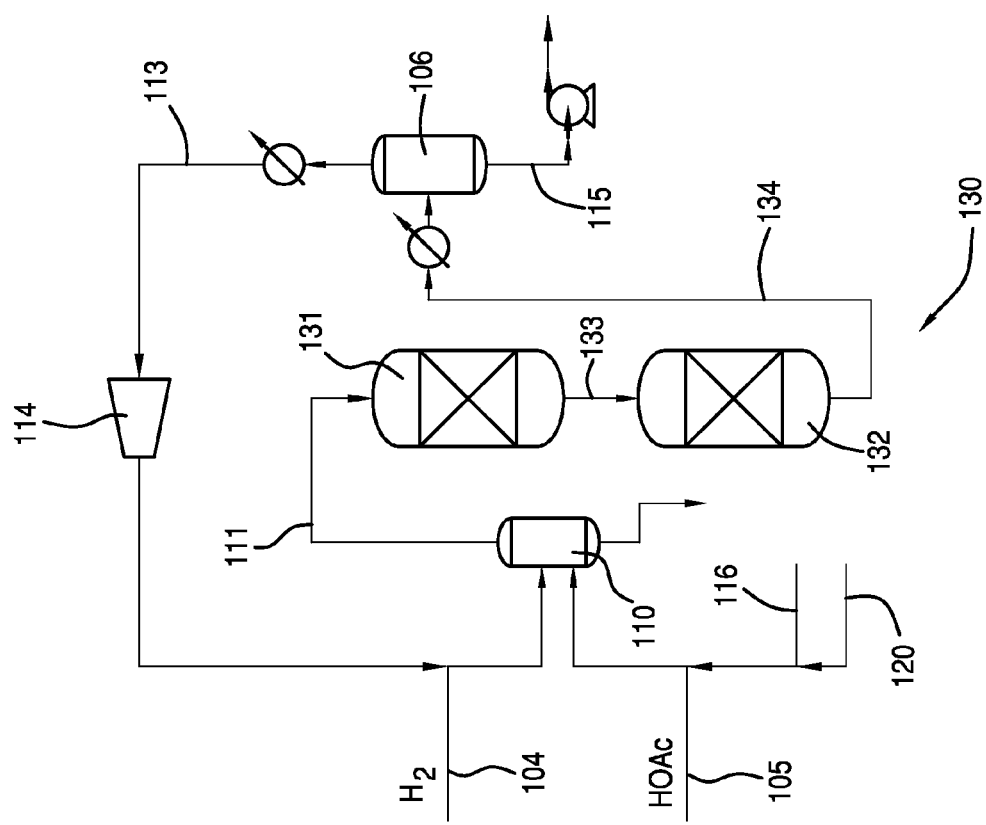
FIG. 2B is a schematic diagram of a reaction zone having a reactor with two reactor regions in accordance with another embodiment of the present invention.

FIGS. 2A and 2B show modified reaction zones 130 and 140, respectively. As discussed above, some embodiments of the present invention may use multiple reactors. In reaction zone 130 of FIG. 2A, vapor feed stream 111 is fed to first reactor 131. Reactor effluent 133 is fed to second reactor 132. Preferably, reactor effluent 133 comprises ethanol and unreacted acetic acid and may have a composition as described above in Table 1. Optionally, fresh reactants (not shown) may be fed to the second reactor 132. Crude ethanol product 134 of second reactor is fed to flasher 106. For purposes of illustration FIG. 2A shows two reactors. In further embodiments, however, there may be more than two reactors, e.g., more than three or more than four. Each of reactors, 131 and 132 of FIG. 2A operate within the reaction conditions stated above.

In the reaction zone 140 of FIG. 2B, vapor feed stream 111 is fed to reactor 141 that comprises multiple reaction regions.

Reactor 141 comprises at least a first reaction region 142 and a second reaction region 143. Each region may have a different catalyst. First reaction region 142 and second reaction region 143 may be separated in reactor 141 as shown in FIG. 2B. In other embodiments, first reaction region 142 and second reaction region 143 overlap and the respective catalysts may be dispersed between the regions. Crude ethanol product 144 of reactor 141, e.g., second reactor region 143, may be fed to flasher 106. Regions 142 and regions 143 operate within the reaction conditions as stated above.

In preferred embodiments, different catalysts may be used in each of the reactors of reactions zones 130 in FIG. 2B or in each of the reaction regions in reaction zones 140 shown in FIG. 2B. Different catalysts may have different metals and/or different supports. In preferred embodiments, the catalyst in first reactor 131 or first reactor region 142 may be cobalt catalyst as described in U.S. Pat. No. 7,608,744, a platinum/tin catalyst as described in U.S. Pub. No. 2010/0029995, or a metal catalyst comprising a basic modifier as described in U.S. Pub. No. 2010/0197959, the entireties of which are hereby incorporated by reference.

In some embodiments, the catalyst in first reactor 131 or first reactor region 142 is a basic catalyst. Suitable metal catalysts that comprise a basic modifier include those having a first metal and an optional second metal. These metals may be the same as those described above with respect to the acidic supported catalysts of the present invention. Preferably, the first metal is Group VIII metal, selected from the group consisting of iron, cobalt, nickel, ruthenium, rhodium, palladium, osmium, iridium, and platinum. The optional second metal preferably may be selected from the group consisting of copper, tin, cobalt, rhenium, and nickel. The catalyst may comprise from 0.1 to 10 wt. % first metal and from 0.1 to 10 wt. % second metal.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The catalyst support may be modified with a support modifier. Preferably, the support modifier is a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. Preferably, the support modifier is a calcium silicate, and more preferably calcium metasilicate ($CaSiO_3$). If the support modifier comprises calcium metasilicate, it is preferred that at least a portion of the calcium metasilicate is in crystalline form. In preferred embodiments that use a basic support modifier, the basic support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

The acidic catalyst of the present invention is preferably used in second reactor 132 or second reactor region 143. In one exemplary embodiment, first reactor 131 or first reactor region 142 may comprise a $SiO_2$—$CaSiO_3$—Pt—Sn catalyst, and the second reactor 133 or second reactor 143 may comprise $SiO_2$—$TiO_2$—Pt—Sn catalyst. In alternative embodiments, the acidic catalyst may be used in first reactor 131 or first reactor region 142.

The acetic acid conversion in first reactor 131 or first reactor region 142 may be relatively lower than that of second reactor 132 or second reactor region 143, respectively. The acetic acid conversion of the first reactor 131 or first reaction region 142 may be at least 10%, e.g., at least 20%, at least 40%, at least 50%, at least 60%, at least 70% or at least 80%. In one embodiment, the acetic acid conversion in first reactor 131 or first reactor region 142 is from 10% to 80% and is lower than the conversion of the unreacted acetic acid in second reactor 132 or second reactor region 143. In second reactor 132 or second reactor region 143, the conversion of the unreacted acetic acid may be increased to at least 70%, e.g., at least 80% or at least 90%. Advantageously, a lower conversion of acetic acid in first reactor 131 or first reactor region 142 allows the unreacted acid of first reactor 131 or first reactor region 142 to be hydrogenated in second reactor 132 or second reactor region 143 without the addition of fresh acetic acid.

The overall ethanol selectivity of the dual reactors shown in FIG. 2A and/or dual reactor regions shown in FIG. 2B may be at least 65%, e.g., at least 70%, at least 80%, at least 85%, or at least 90%. Ethyl acetate, which may be produced by the first reactor 131 or first reactor region 142, may be consumed in the second reactor 132 or second reactor region 143.

Finished Ethanol

The finished ethanol composition obtained by the processes of the present invention preferably comprises from 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 6.

TABLE 6

FINISHED ETHANOL COMPOSITIONS

| Component | Conc. (wt. %) | Conc. (wt. %) | Conc. (wt. %) |
| --- | --- | --- | --- |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol is from 80 to 1,000 wppm, e.g., from 95 to 1,000 wppm, from 100 to 700 wppm, or from 150 to 500 wppm. In one embodiment, the finished ethanol composition preferably is substantially free of acetaldehyde and may comprise less than 8 wppm of acetaldehyde, e.g., less than 5 wppm or less than 1 wppm.

The finished ethanol composition produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid or reacted with polyvinyl acetate. The finished ethanol composition may be dehydrated to produce ethylene. Any of known dehydration catalysts can be employed in to dehydrate ethanol, such as those described in copending U.S. application Ser. No. 12/221,137 and U.S. application Ser. No. 12/221,138, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, the following examples are provided below.

EXAMPLES

Example 1

Figure 3:
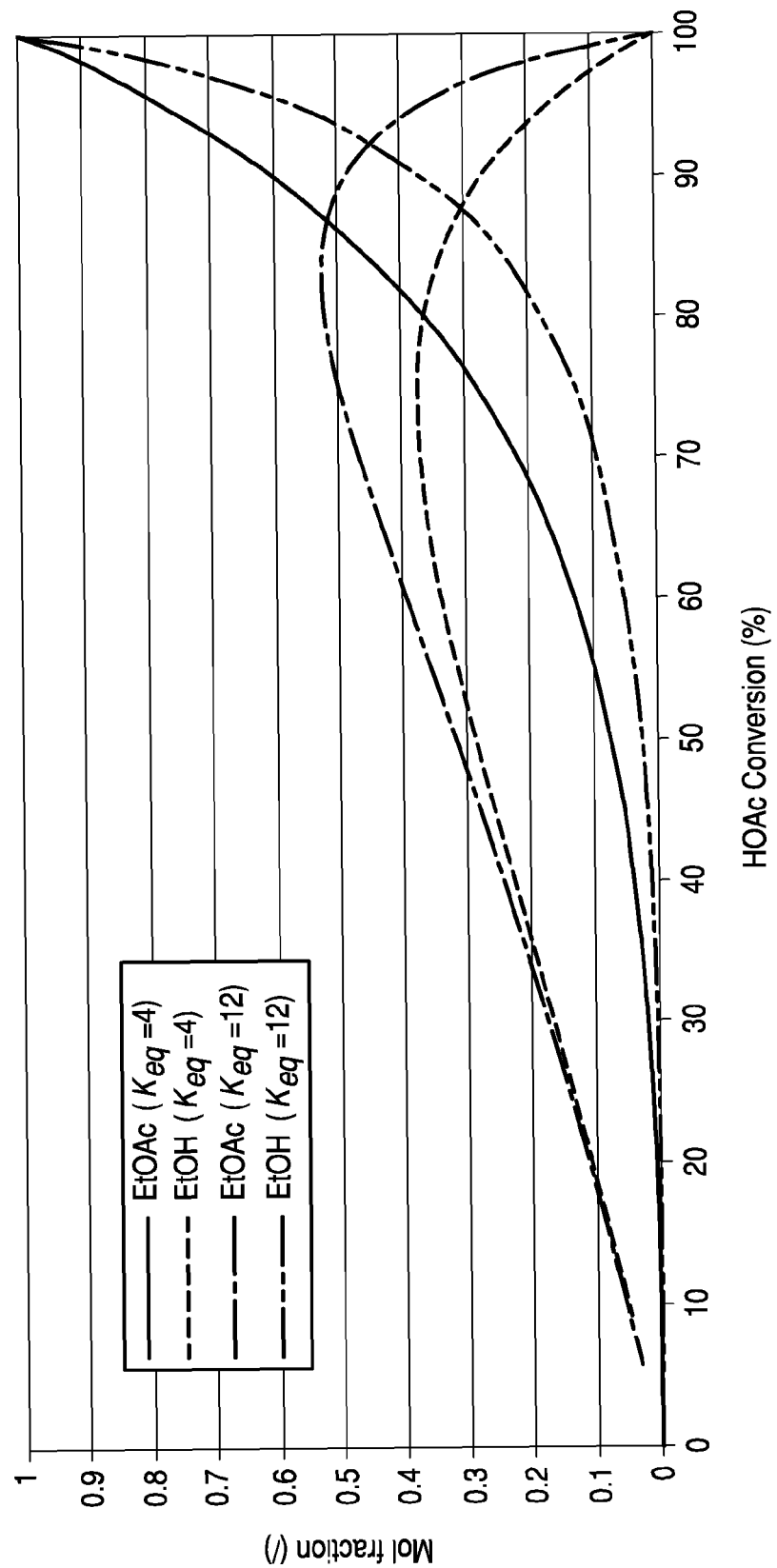
FIG. 3 is a graph of acetic acid conversion in accordance with an example of the present invention.

Acetic acid was hydrogenated in the present of an acidic catalyst comprising $SiO_2$—$TiO_2$(10 wt. %)-Pt(1.6 wt. %)-Sn (1.0 wt. %). There were 2 runs with this catalyst in a reactor at 200 psig, 250° C. First run was at 4500 $hr^{-1}$ GHSV, and the second run was at 2200 $hr^{-1}$ GHSV. In FIG. 3, the theoretical calculations for a $K_{eq}$ of 4 and for a $K_{eq}$ of 12. As indicated in FIG. 3, the amount of ethyl acetate at lower acetic acid conversion is greater than that of ethanol. However, at higher acetic acid conversions, the kinetics of the equilibrium reaction surprisingly drive the ethyl acetate content lower and increase the ethanol content. Table 7 summarizes the results.

TABLE 7

| Run | GHSV | HOAc Conversion | Selectivity (mol %) EtOH | EtOAc |
|---|---|---|---|---|
| 1 | 4500 $hr^{-1}$ | 71.9% | 58.8% | 40.6% |
| 2 | 2200 $hr^{-1}$ | 92.9% | 79.2% | 20.4% |

Example 2

Figure 4:
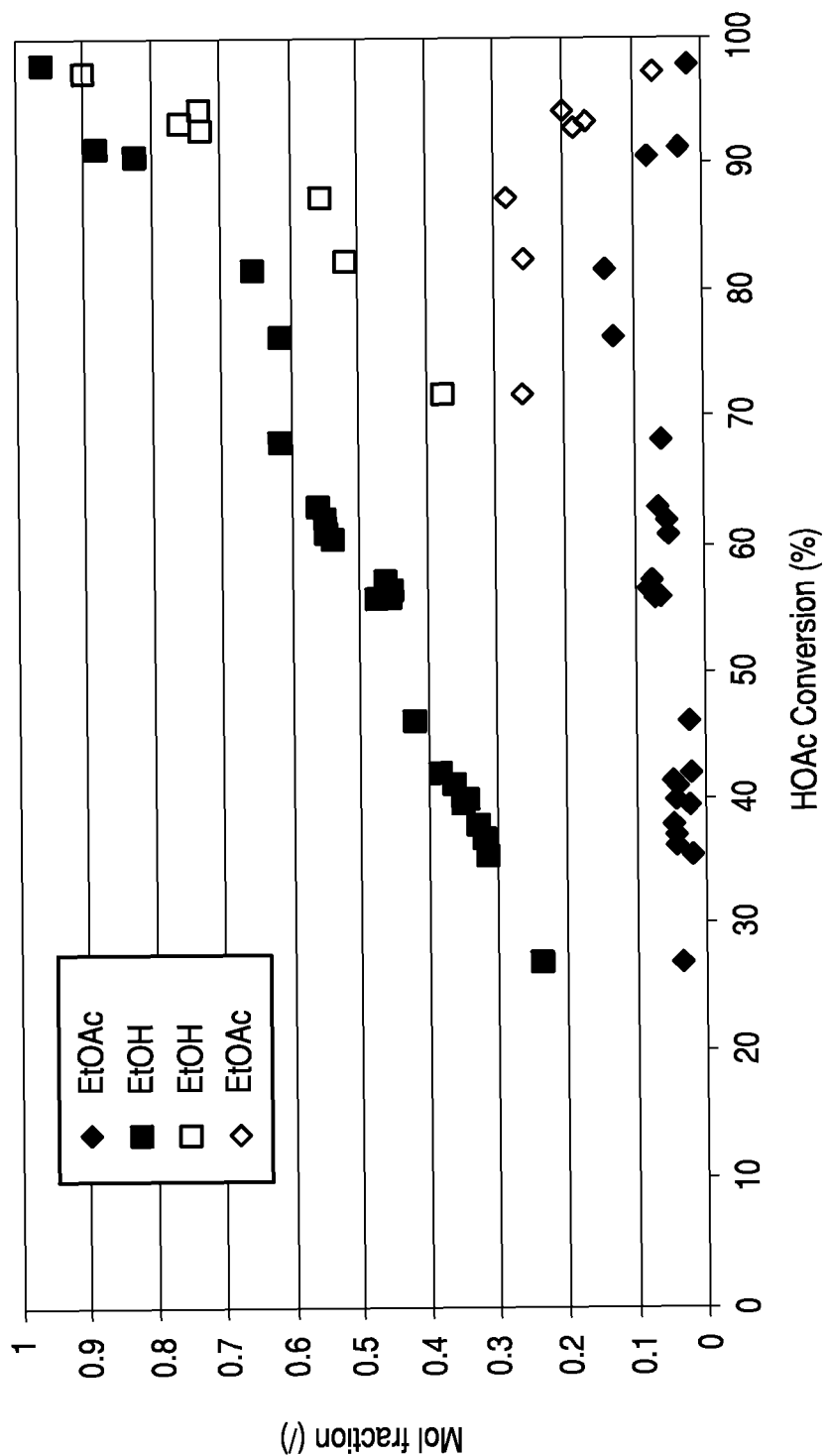
FIG. 4 is a graph of acetic acid conversion of different catalysts in accordance with an example of the present invention.

Acetic acid was hydrogenated in the present of an acidic catalyst comprising $SiO_2$—$TiO_2$(10 wt. %)-Pt(1.6 wt. %)-Sn (1.0 wt. %) and an acidic catalyst comprising $SiO_2$—$Al_2O_3$(7 wt. %)-Pt(1.6 wt. %)-Sn(1.0 wt. %). Each hydrogenation was performed several times under different acetic acid conversion levels. The results are compared in FIG. 4. At lower conversions, the $SiO_2$—$Al_2O_3$(7 wt. %)-Pt(1.6 wt. %)-Sn(1.0 wt. %) catalyst showed increased selectivity to ethanol. However, at higher conversions, the $SiO_2$—$TiO_2$(10 wt. %)-Pt(1.6 wt. %)-Sn(1.0 wt. %) catalyst showed similar selectivity to ethanol. In addition, surprisingly and unexpectedly, the productivity of the acidic catalyst at high acetic acid conversion showed a significant improvement.

Example 3

The acidic catalyst comprising $SiO_2$—$Al_2O_3$(7 wt. %)-Pt(1.6 wt. %)-Sn(1.0 wt. %) from Example 2 was also used to hydrogenate acetic acid in several runs under the following different reaction conditions set forth in Table 8.

TABLE 8

| Run | Pressure | Temperature | GHSV | HOAc Conversion | Selectivity (mol %) EtOH | EtOAc |
|---|---|---|---|---|---|---|
| 1 | 200 psig | 250° C. | 4500 $hr^{-1}$ | 87.5 | 65.8 | 33.4 |
| 2 | 200 psig | 250° C. | 2200 $hr^{-1}$ | 93.4 | 81.4 | 18.0 |
| 3 | 250 psig | 300° C. | 4500 $hr^{-1}$ | 94.3 | 75.4 | 20.8 |
| 4 | 250 psig | 300° C. | 1300 $hr^{-1}$ | 97.3 | 89.2 | 7.2 |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising
hydrogenating acetic acid in the presence of a first catalyst to form an intermediate product comprising ethanol and unreacted acetic acid; and
hydrogenating the unreacted acetic acid in the present of a second catalyst to form ethanol, wherein the second catalyst comprises a first metal on an acidic support selected from the group consisting of
an acidic support material selected from the group consisting of iron oxide, alumina, silica/alumina, titania, zirconia, and mixtures thereof, and
a support material modified with an acidic modifier.

2. The process of claim 1, wherein the first catalyst comprises a catalyst comprising one or more metals, a siliceous support, and at least one basic support modifier.

3. The process of claim 2, wherein the at least one basic support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

4. The process of claim 2, wherein the silicaceous support is selected from the group consisting of silica, silica/alumina, calcium metasilicate, pyrogenic silica, high purity silica and mixtures thereof.

5. The process of claim 1, wherein the hydrogenating acetic acid is conducted in a first reactor and the hydrogenating of the unreacted acetic acid is conducted in a second reactor.

6. The process of claim 5, wherein at least 10% of the acetic acid is converted in the first reactor, and at least 70% of the unreacted acetic acid is converted in the second reactor.

7. A process for producing ethanol, comprising
hydrogenating acetic acid in the presence of a first catalyst and a second catalyst in a reactor to form ethanol, wherein the second catalyst comprises a first metal on an acidic support selected from the group consisting of
an acidic support material selected from the group consisting of iron oxide, alumina, silica/ alumina, titania, zirconia, and mixtures thereof, and
a support material modified with an acidic modifier.

8. The process of claim 7, wherein the first catalyst is in a first reactor region and the second catalyst is in a second reactor region, wherein the first reactor region and the second reactor region are separated.

9. The process of claim 7, wherein the first catalyst comprises a catalyst comprising one or more metals, a silicaceous support, and at least one basic modifier.

10. The process of claim 9, wherein the at least one basic support modifier is selected from the group consisting of (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof.

11. The process of claim 9, wherein the silicaceous support is selected from the group consisting of silica, silica/alumina, calcium metasilicate, pyrogenic silica, high purity silica and mixtures thereof.

\* \* \* \* \*